United States Patent [19]
Hui et al.

[11] Patent Number: 5,716,322
[45] Date of Patent: Feb. 10, 1998

[54] MEDICAL INSTRUMENT AND METHOD FOR LUBRICATION AND STERILIZATION THEREOF

[75] Inventors: Henry Hui, Laguana Niguel; Leslie A. Feldman, Calabasas Hills; Hung P. Nguyen, Torrance; Debra Timm, Foothill Ranch; Ron Albers, Irvine, all of Calif.

[73] Assignee: Johnson & Johnson Medical, Inc., Arlington, Tex.

[21] Appl. No.: 614,706

[22] Filed: Mar. 13, 1996

[51] Int. Cl.⁶ ............................................ A61B 1/04
[52] U.S. Cl. .................... 600/133; 600/101; 600/160; 365/115; 365/117
[58] Field of Search .................... 600/101, 114, 600/133, 160; 385/115, 116, 117; 134/2, 3, 28

[56] References Cited

U.S. PATENT DOCUMENTS

| | | | |
|---|---|---|---|
| 4,035,210 | 7/1977 | Ohyoshi et al. | 156/645 |
| 4,506,544 | 3/1985 | Shimizu . | |
| 4,784,464 | 11/1988 | Ouchi . | |
| 5,073,048 | 12/1991 | Adachi et al. . | |
| 5,208,890 | 5/1993 | Kohler et al. . | |
| 5,394,864 | 3/1995 | Kobayashi et al. | 128/4 |

*Primary Examiner*—Beverly M. Flanagan

[57] ABSTRACT

Medical instruments incorporating solid lubricants are shown to survive an oxidizing sterilization process if they employ solid lubricants free from disulfide and diselenide compounds such as molybdenum disulfide and the instrument is kept free from such compounds. PTFE, powdered graphite and boron nitride are preferred solid lubricants. Of particular importance are flexible endoscope employing solid lubricants on fiber optic bundles encased in elastomeric coverings.

16 Claims, 1 Drawing Sheet

MEDICAL INSTRUMENT AND METHOD FOR LUBRICATION AND STERILIZATION THEREOF

BACKGROUND

1. Field of the Invention

The present invention relates generally to medical instruments having lubricated surfaces thereon and to a method for lubricating such surfaces and sterilizing the instruments.

2. State of the Prior Art

Delicate medical instruments, such as flexible endoscopes and the like, are notoriously difficult to sterilize. Flexible endoscopes have elastomeric parts that cannot survive the intense heat of steam sterilization typically used in the hospital and clinical environment. Typically, these instruments are now dipped into baths of liquid sterilants, with some of the liquid being forced through the long lumens within the endoscopes. Such processes have limitations. For instance, the high toxicity of many of the preferred liquid sterilants classifies them as hazardous waste after the procedure and makes them dangerous to work with. Also, liquid does not penetrate small crevices within an instrument as well as gaseous phase sterilants such as high pressure steam.

Gaseous sterilization with strong oxidizing agents such as hydrogen peroxide is a well established method for sterilizing delicate instruments such as flexible endoscopes. Ethylene oxide (EtO) gas is one such sterilant. However, it must be handled carefully as it is extremely toxic. One particularly effective technology is hydrogen peroxide gas plasma sterilization such as that provided by the STERRAD systems of Advanced Sterilization Products division of Johnson & Johnson Medical, Inc. In this type of system, instruments are placed into a sealed chamber and exposed to an atmosphere containing hydrogen peroxide in the gaseous phase. The chamber is placed under a vacuum to encourage the hydrogen peroxide vapor to reach all areas of the instrument. Once the vapor has reached all surfaces on the instruments in the chamber, an electromagnetic field is applied to the chamber driving the hydrogen peroxide into the plasma phase of matter. This enhances the sterilizing effect of the hydrogen peroxide. Further, when the field is released, the free radicals in the plasma recombine to form water and oxygen, thereby leaving no harmful residuals.

However, when flexible endoscopes and certain other delicate instruments were subjected to this type of process, many experienced rapid degradation of their elastomeric parts. This was curious as it was not thought that the hydrogen peroxide would affect such parts. Even more perplexing was the apparent random nature of the problem. Many theories were propounded, including some unknown interaction between the hydrogen peroxide, the plasma state and the elastomers. The present inventors have discovered that the degradation stems not from the action of the oxidizer on the elastomer, but from the action of the oxidizer on lubricating substances in instruments which in turn form compounds which degrade the elastomers. Certain lubricants found in endoscopes and other instruments breakdown in the oxidizing environment of the hydrogen peroxide vapor to form acids which can damage the elastomeric parts of delicate medical instruments. The lubricants are members of the class of metal dichalcogenides, such as molybdenum disulfide. These lubricants are also sometimes incorporated into nylon materials which are also employed in certain medical instruments.

SUMMARY OF THE INVENTION

The present invention is based upon the finding that by removing metal dichalcogenides from a medical instrument and replacing them with another suitable lubricant, one can both lubricate the instrument and sterilize the instrument in an oxidizing atmosphere without degrading the lubricant or creating low pH substances capable of damaging the instrument.

A method for lubricating and sterilizing a medical instrument according to the invention comprises lubricating a surface on the medical instrument with a solid lubricant free from disulfide compounds. The instrument, the surface thereon and the lubricant are then repeatedly sterilized by exposure to an oxidizing chemical atmosphere. The medical instrument is protected from corrosive acids by keeping the medical instrument surface free from disulfide compounds whereby the absence of disulfide compounds limits the formation of corrosive acids in the oxidizing chemical atmosphere to protect the medical instrument.

Preferably the lubricant comprises PTFE, powdered graphite or boron nitride. The oxidizing chemical preferably comprises hydrogen peroxide. The medical instrument may comprise a flexible endoscope having a fiber optic bundle lubricated with the lubricant and an elastomeric cover surrounding the fiber optic bundle. Preferably, the instrument is also kept free of diselenide compounds.

A medical instrument according to the invention comprises a surface to be lubricated, and a solid lubricant, free from disulfide compounds, on the surface, wherein the medical instrument is free of disulfide compounds. The medical instrument can be repeatedly exposed to an oxidizing chemical atmosphere without damage thereto as the absence of disulfide compounds prevents the formation of corrosive acids in the oxidizing chemical atmosphere to protect the medical instrument.

Preferably, the medical instrument further comprises a fiber optic bundle and an elastomeric covering thereabout with the lubricant on the fiber optic bundle.

BRIEF DESCRIPTION OF THE DRAWINGS

FIG. I is a perspective view of a flexible endoscope insertion portion having a fiber optic bundle within a flexible elastomeric coating.

DETAILED DESCRIPTION

Figure 1:
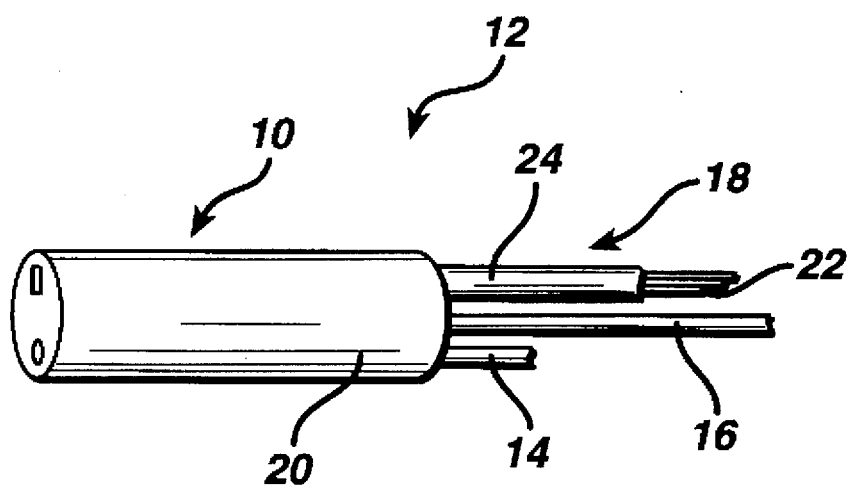

There is a fairly wide range of possible solid lubricant materials available for industrial applications. These solid lubricants can be divided into four main classes: layered solids, polymers, soft metals, and low shear strength solids. Some examples are shown in the following table.

| Solid Lubricants | Typical Examples |
| --- | --- |
| 1. Layered solids | Dichalcogenides ($MoS_2$, $WS_2$, $WSe_2$, etc.) |
| | Graphite |
| | Boron nitride |
| | $CdCl_2$, $PbCl_2$ |
| | Pthalocyanines |
| 2. Polymers | PTFE (Teflon) |
| | FEP |
| | Polyacetal |
| | Polyimide |
| | UHMWPE |
| | Phenolic and epoxy resins |
| 3. Soft metals | Au, Ag, Pb, In, Ba |
| 4. Low shear strength solids | Oxides: Cd, Co, Zn |
| | Sulfides: Bi, Cd |
| | Fluorides: Ca, Li, Ba, rare earths |

As a lubricant material, molybdenum disulfide ($MoS_2$) is used in a variety of industrial applications. Molybdenum disulfide is found as a naturally occurring mineral (molybdenite), and belongs to a class of layered structure or lamellar compounds, a number of which my have useful lubrication properties. Molybdenum disulfide owes its lubricant properties to its hexagonal crystal structure with layers of Mo sandwiched between layers of S on each side. The bonding of Mo and S atoms within the sandwich layers is strong compared to the bonding between the S layers in adjacent sandwich layers. This weak bonding between layers allows for easy slippage and accounts for the lubricating properties.

Molybdenum disulfide is used in many applications because it has a low coefficient of friction and negligible vapor pressure, and consequently it does not evaporate over a long period of time. It is also insensitive to temperature, so that its lubricating and other properties do not vary significantly at different temperatures. It is stable at elevated temperature in nonoxidizing conditions, and can resist oxidation in air up to approximately 500° C. Molybdenum disulfide can be applied by burnishing (rubbing) a powder or solid piece of lubricant material onto a component surface. The lubricant is loosely adhered to the surface. One disadvantage is that it can become nonuniformly distributed. Another disadvantage is that it can also become rubbed off, leaving uncoated regions, and it is difficult to resupply the area, unlike liquid lubricants, which can flow back to the exposed area. However, for moderate mechanical cycle life and moderate stress on the contacting surfaces, solid lubricants can have advantages in terms of low friction, low vapor pressure, temperature insensitivity, and good performance in vacuum.

Molybdenum disulfide is moisture sensitive, and should preferably be used in a low moisture, low humidity environment. Molybdenum disulfide carries significant toxicity hazards, including potentially harmful effects if swallowed, inhaled and/or absorbed through the skin. It causes eye irritation, skin irritation, mucous membrane and respiratory tract irritation, and it has mutagenic effects. Because it works best in a dry environment, it is a good solid lubricant for vacuum applications.

We have identified that the solid lubricant molybdenum disulfide is used as an additive to nylon 6/6 in NYLATRON (a commercial grade of nylon) available from the Polymer Corporation of Reading, Pa. Many bearings are formed of NYLATRON and it is used in the manufacture of the body of some diathermy probes for ophthalmic applications.

Molybdenum disulfide is also found in many flexible endoscopes. FIG. 1 depicts an insertion portion 10 of a flexible endoscope 12. A lumen 14, a steering mechanism 16 and a fiber optic bundle 18 are encased in an airtight elastomeric outer covering 20. The fiber optic bundle 18 comprises a large number of individual optical fibers 22 and a sheath 24 surrounding the fibers 22. Generally, the sheath 24 is formed of silicone. Molybdenum disulfide lubricates the fiber optic bundle 18 to reduce friction between the individual optical fibers 22 as they slide against each other during the maneuvering of the insertion portion 10. Molybdenum disulfide is generally dispersed throughout the interior of the insertion portion 10 so that it also lubricates the steering mechanism 16, the lumen 14 and the covering 20 as they slide against each other.

Reduction in lubricity will result in breakage of fibers 22 thereby diminishing light throughput and image quality. Replacement of the fiber optic bundle 18 in the flexible endoscope 12 is prohibitively expensive and may cost upward of $4,500 for repair.

During sterilization under vacuum, a leak detection port, not shown, is opened to place the interior of the endoscope insertion portion 10 into pressure communication with the outside atmosphere. This prevents the air trapped within the outer covering 20 from exerting excessive pressure against the outer covering 20. However, this also allows the sterilizing gas to enter the interior of the endoscope insertion portion 10 and react with the molybdenum disulfide lubricant.

In U.S. Pat. No. 4,506,544, issued Mar. 26, 1985, and incorporated herein by reference, Shimizu describes a flexible endoscope and its leak detection port in some detail. In U.S. Pat. No. 4,784,464, issued Nov. 15, 1988, and incorporated herein by reference, Ouchi describes in detail an endoscope fiber bundle lubricated with molybdenum disulfide lubricant.

Since the insertion portion 10 is inserted inside the body, the material choice is critical. The material must be flexible and biocompatible. Polyurethanes are commonly used for the thin outer covering 20 the insertion tube. These materials offer a good combination of flexibility, strength, durability, and stability, as well as biocompatibility. However, when the outer covering 20 is formed of polyurethane vastly greater mounts of hydrogen peroxide enter the interior of the insertion portion by diffusion through the covering 20 than would enter through the pressure equalization port.

Hydrogen peroxide gas plasma sterilization systems, such as the STERRAD System, use hydrogen peroxide in vapor form at low pressure (less than 14 Torr pressure of 59% hydrogen peroxide) at a nominal operating temperature of 45° C. in the sterilization process. Under these conditions metal dichalcogenides, such as molybdenum disulfide, will react with hydrogen peroxide. The reaction is illustrated by the following equation:

$$MoS_2+(4+x) H_2O_2 \rightarrow MoO_x+(4+x) H_2O+2 SO_2\uparrow$$

Visually, samples of molybdenum disulfide powder exposed to gas plasma hydrogen peroxide sterilization for several cycles change rapidly from their normal gray color to a mixture of yellow and blue (probably corresponding to various oxidation states of molybdenum). Samples may begin to emit a sharp, pungent odor, possibly corresponding to traces of sulfur oxides.

As discussed above, sulfur oxides are potential by-products of chemical oxidation of molybdenum disulfide by hydrogen peroxide. In addition, the oxides may react with excess water to form sulfurous acid:

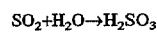

$$SO_2+H_2O \rightarrow H_2SO_3$$

It is also possible that the sulfur may be further oxidized, giving rise to $SO_3$ and sulfuric acid. The exact stoichiometry for reaction of the solid lubricants is not known, but samples of powdered disulfide lubricants processed in open containers for five cycles have shown measured pH levels of less than 1.0, which is highly acidic. In addition, although some of the sulfur may escape as vapor, the fact that test samples of molybdenum disulfide powder did not lose weight but increased in weight after processing, evidence that the sulfur is being retained as oxides and sulfurous acids with the addition of water.

The acid by-products in particular can act to degrade certain materials. Some examples of materials which have been observed to degrade in combination with molybdenum disulfide after hydrogen peroxide gas plasma processing are polyurethane and silicone elastomers and molybdenum disulfide-filled nylon (such as the tradename NYLATRON mentioned earlier). In the case of polyurethane and silicone materials, the lubricant powder has been applied as a dry powder or alcohol slurry and allowed to dry onto the surface.

In the case of NYLATRON, the material is a nylon 6/6 formulation blended together with a few percent of molybdenum disulfide. NYLATRON was observed to undergo slow surface degradation, with discoloration from dark gray to a light brownish-yellow or tan, and gradual pitting, powdering and chipping of the surface.

For the elastomers, the effects include embrittlement, loss of strength and elongation, blistering, and formation of liquid residues. Silicone tubing breaking strengths were observed to decrease from 1400 psi to 600 psi after two cycles (over 50% reduction in strength) on close contact with molybdenum disulfide. Polyurethane tubing has been observed to undergo degradation and cracking as a result of close contact with molybdenum disulfide during processing. Of particular interest is a common type of flexible endoscope device construction as shown in FIG. 1 where hydrogen peroxide first diffused through the polyurethane outer cover 20 leading to reaction with molybdenum disulfide, causing eventual failure of the outer cover 20.

In addition to hydrogen peroxide gas plasma, there are other sterilization methods which employ oxidization processes or strong oxidizers for sterilization. Some other oxidizing sterilants and methods include ozone ($O_3$), chlorine dioxide ($ClO_2$), EtO, hydrogen peroxide vapor without plasma, and peracetic acid. These oxidizing sterilants are expected to react similarly with molybdenum disulfide and cause material degradation.

We have tested various lubricant materials for compatibility with some particular polymers which are used in medical devices (polyurethane and silicone). These lubricants included PTFE, boron nitride, and graphite. They fall under the categories of polymer and layered structure lubricants, and are all readily available in powered form. The layered compounds all function similarly, having a weak bond between the planar layers which allows easy slippage in the two directions parallel to the layers.

Testing of powdered lubricants of graphite, BN and Teflon was done by encapsulating lubricants in two types of polyurethane tubing, a soft ester-based and a hard ether-based composition. Samples of both tubing types containing each of three lubricant powders (six samples in total) were prepared by sealing the ends with a hot melt adhesive. The samples were then processed for 100 cycles in the STERRAD hydrogen peroxide gas plasma system. No degradation was found for any of the samples, in contrast to typical findings of 11–13 cycles for molybdenum disulfide lubricant encapsulated in the soft polyurethane tubing. Thus, it appears that degradation of the polyurethane was eliminated with the lubricants, and all three may be considered as substitutes for molybdenum disulfide for this application.

Graphite lubricant contains a thin layer of absorbed moisture on its surface which gives reduced shear strength between the molecular layers and a low friction coefficient. At low pressure (below $10^{-2}$ Pa or 0.1 millitorr) the absorbed moisture desorbs from the graphite and its friction coefficient rises significantly. However, with short vacuum exposure, or vacuum above 0.1 millitorr (consistent with the STERRAD hydrogen peroxide gas plasma type system), graphite friction properties should be unaffected. Further, powdered PTFE may experience a small degree of clumping which will not significantly affect its performance, Other lubricants in the same category as molybdenum disulfide (layered dichalcogenides such as $WS_2$, $WSe_2$ and $NbSe_2$) were investigated. This was done to compare them with molybdenum disulfide, according to whether they also react in a hydrogen peroxide gas plasma system and whether they cause similar degradation effects on polymers. Testing was done on mechanical strength of silicone tubing (Dew Corning SILASTIC) after contamination with solid lubricants and STERRAD hydrogen peroxide gas plasma system processing. Pieces of 3/16 in. diameter tubing were slurry coated and dried with coatings of $MoS_2$, $WS_2$, $WSe_2$ and $NbSe_2$ lubricants. After two cycles mechanical strength measurements using an INSTRON tensile strength testing machine showed the following results.

| Lubricant Coating | Tensile Strength (psi) |
|---|---|
| Uncoated and unprocessed | 1393 |
| | 1411 |
| $MoS_2$ | 622 |
| $WS_2$ | 320 |
| | 252 |
| $NbSe_2$ | 1413 |
| | 1297 |
| $WSe_2$ | 1400 |
| | 1408 |

Thus, metal sulfides lead to deterioration of the polymers, probably through similar acid forming mechanisms. The diselenides, however, did not appear to lead to degradation of the silicone, although in the tests the diselenides showed significant lightening in color, probably due to reaction with hydrogen peroxide because the coated surfaces were directly exposed to the sterilant. In general, neither the disulfide nor the diselenide would be recommended on the basis of both long-term stability and degradation effects.

As the previous discussion shows, the use of molybdenum disulfide solid lubricants in devices for sterilization by oxidizing processes or agents such as hydrogen peroxide may lead to degradation of the molybdenum disulfide, which can lead to loss of lubrication properties and possible degradation of associated materials. It is recommended that molybdenum disulfide be avoided where a) the molybdenum disulfide can be directly or indirectly exposed to hydrogen peroxide (even in very small mounts) and b) molybdenum disulfide is in close contact with materials which will be susceptible to degradation.

While the invention has been particularly described in connection with specific embodiments thereof, it is to be understood that this is by way of illustration and not of limitation, and that the scope of the appended claims should be construed as broadly as the prior art will permit.

What is claimed is:

1. A method for lubricating and sterilizing a medical instrument comprising the steps of:

lubricating a surface on the medical instrument with a solid lubricant free from disulfide compounds;

repeatedly exposing the medical instrument, the surface thereon and the lubricant to an oxidizing chemical atmosphere;

protecting the medical instrument from corrosive acids by keeping the medical instrument surface free from disulfide compounds whereby the absence of disulfide compounds prevents the formation of corrosive acids in the oxidizing chemical atmosphere to protect the medical instrument.

2. A method according to claim 1 and further comprising the step of selecting the lubricant from the group consisting of: PTFE, powdered graphite and boron nitride.

3. A method according to claim 2 wherein the lubricant comprises PTFE.

4. A method according to claim 2 wherein the lubricant comprises powdered graphite.

5. A method according to claim 2 wherein the lubricant comprises boron nitride.

6. A method according to claim 1 wherein the oxidizing chemical is hydrogen peroxide.

7. A method according to claim 2 wherein the oxidizing chemical is hydrogen peroxide.

8. A method according to claim 1 wherein the medical instrument comprises a flexible endoscope having a fiber optic bundle comprising the surface and an elastomeric cover surrounding the fiber optic bundle.

9. A method according to claim 1 wherein the medical instrument comprises a flexible endoscope having a fiber optic bundle comprising the surface and an elastomeric cover surrounding the fiber optic bundle.

10. A method according to claim 9 wherein the oxidizing chemical is hydrogen peroxide.

11. A method according to claim 1 and further comprising the step of keeping the medical instrument surface free from diselenide compounds whereby the absence of diselenide compounds prevents the formation of corrosive acids in the oxidizing chemical atmosphere to protect the medical instrument.

12. A medical instrument comprising:

a surface to be lubricated;

a solid lubricant on the surface, the lubricant being selected from the group consisting of: PTFE, powdered graphite and boron nitride;

wherein the medical instrument is free of disulfide compounds; and wherein the medical instrument can be repeatedly exposed to an oxidizing chemical atmosphere without damage thereto; and whereby the absence of disulfide compounds prevents the formation of corrosive acids in the oxidizing chemical atmosphere to protect the medical instrument.

13. A medical instrument according to claim 12 wherein the medical instrument further comprises a flexible endoscope having a fiber optic bundle and an elastomeric outer covering thereabout and wherein the surface to be lubricated comprises an inner surface of the outer covering.

14. A medical instrument according to claim 13 wherein the lubricant comprises PTFE.

15. A medical instrument according to claim 13 wherein the lubricant comprises powdered graphite.

16. A medical instrument according to claim 13 wherein the lubricant comprises boron nitride.

* * * * *